US007592159B2

(12) United States Patent
Stahl

(10) Patent No.: US 7,592,159 B2
(45) Date of Patent: *Sep. 22, 2009

(54) ANTIBIOTIC ALTERNATIVES

(75) Inventor: Chad H. Stahl, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 266 days.

This patent is subject to a terminal disclaimer.

(21) Appl. No.: 11/327,713

(22) Filed: Jan. 6, 2006

(65) Prior Publication Data

US 2006/0154338 A1 Jul. 13, 2006

Related U.S. Application Data

(63) Continuation-in-part of application No. PCT/US2005/008512, filed on Mar. 15, 2005.

(60) Provisional application No. 60/553,209, filed on Mar. 15, 2004.

(51) Int. Cl.
*C12P 21/00* (2006.01)
*C12Q 1/68* (2006.01)
*C12N 15/00* (2006.01)

(52) U.S. Cl. .................. 435/71.1; 435/6; 435/69.1

(58) Field of Classification Search ............... None
See application file for complete search history.

(56) References Cited

U.S. PATENT DOCUMENTS 4,929,445 A * 5/1990 Vandenbergh et al. ...... 424/115
5,965,128 A 10/1999 Doyle et al.

FOREIGN PATENT DOCUMENTS

| EP | 1 475 432 A1 | 10/2004 |
|---|---|---|
| WO | WO 94/26132 | 11/1994 |
| WO | WO 95/06663 | 3/1995 |
| WO | WO 2005/089812 A2 | 9/2005 |

OTHER PUBLICATIONS

Patton et al. Inhibitory of Colicin E1 against Listeria monocytogenes. J. of Food Protection 70(5): 1256-1262, 2007.*
Wooley et al. Inhibition of *Salmonella typhimurium* in the chicken intestinal tract by a transformed avirulent avian *Escherichia coli*. Avian Diseases 43: 245-250, 1999.*
Eraso et al. Anaerobic Control of Colicin E1 Production. J. Bac. 174(15): 5101-5109, 1992.*
Adams et al. Frequency-Dependent Selection for Plasmid-Containing Cells of *Escherichia Coli*. Genetics. Apr. 1979;91(4):627-637.*
McCormick, J.K. et al. "Colicin V can be produced by lactic acid bacteria", Letters in Applied Microbiology, Jul. 1999, vol. 29, No. 1., p. 37-41, XP002336015.
Cregg, J.M., et al., "Recombinant Protein Expression in Pichia Pastoris", Molecular Biotechnology, Totowa, NJ, US, vol. 16, No. 1, Sep. 2000, pp. 23-52, XP001078868.
Hinnen, A., et al., "Transformation of yeast", Proceedings of the National Academy of Sciences of the USA, 1989 US, vol. 75, No. 4, 1978, pp. 1929-1933, XP002336016.
Braun, V., et al., "Colicins: Structures, modes of action, transfer through membranes, and evolution." Archives of Microbiology. 1994, vol. 161, No. 3, 1994, pp. 199-206, XP008049770.
Murinda Shelton E., et al., "Evaluation of colicins for inhibitory activity against diarrheagenic *Escherichia coli* strains, including serotype 0157:H7", Applied and Environmental Microbiology, vol. 62, No. 9, 1996, pp. 3196-3202, XP002345269.
Trcja J, Smarda J:, "Is there any function for colicinogeny in the post-weaning diarrhea of piglets?", Veterinarni Medicina, vol. 48, No. 7, Jul. 2003, pp. 190-198, XP002345379.
Smith H.W., et al., "Treatment of experimental *Escherichia coli* infection in mice with colicine V", J. of Medical Microbiology 1977 UK, vol. 10, No. 4, 1977, pp. 479-482, XP008052598.
Litinskii Y.I. et al., "Effect of colicin V on S. sonnei in vivo and in tissue culture", J. of Hygiene, Epidemiology, Microbiology, and Immunology, 1977, vol. 21, No. 1, 1977, pp. 42-48, XP008052615.
Verdonck F et al., "Different kinetic of antibody responses following infection of newly weaned pigs with an F4 enterotoxigenic *Escherichia coli* strain or an F18 verotoxigenic *Escherichia coli* strain", Vaccine, vol. 20, No. 23-24, Jul. 26, 2002, pp. 2995-3004, XP002345271.

(Continued)

*Primary Examiner*—Christopher S. F. Low
*Assistant Examiner*—Michele K. Joike
(74) *Attorney, Agent, or Firm*—McKee, Voorhees & Sease, P.L.C.

(57) ABSTRACT

The present invention relates to two recombinant colicin expression systems, one utilizing a yeast expression system that produces a protein that is inexpensive to purify, and the other utilizing a plasmid expression system to be used as a probiotic culture. The recombinant colicins provide effective alternatives to conventional antibiotics and may be used to improve the efficiency of pork production, and the safety of its products.

5 Claims, 11 Drawing Sheets

OTHER PUBLICATIONS

Callway T.R et al., "Colicin concentrations inhibit growth of *Escherichia coli* 0157:H7 in vitro", J. of Food Protection, vol. 67, No. 11, 11, 2004, pp. 2603-2607, XP008049775.

Stahl, Chad H., et al., "Inhibitory activities of colicins against *Escherichia coli* strains responsible for postweaning diarrhea and edema disease in swine", Antimicrobial Agents and Chemotherapy, vol. 48, No. 8, 08, 2004, pp. 3119-3121, XP002345272.

Brandis, H., "Die Natur der Bacteriocine", Naturwissenschaften, vol. 62, No. 1, 1975, pp. 22-28.

Patton, Brenda S. et al., "Inhibitory activity of colicin E1 against Listeria monocytogenes" Journal of Food Protection< vol. 70, No. 5, May 2007, pp. 1256-1262.

Stahl, Chad H. et al., "Inhibitory activities of colicins against *Escherichia coli* strains responsible for postweaning diarrhea and edema disease in swine" Antimicrobial Agents and Chemotherapy, American Society for Microbiology, Washington, DC., vol. 48, No. 8, Aug. 2004, pp. 3119-3121.

Vignolo, G. et al., "Control of Listeria monocytogenes in ground beef by 'Lactocin 705', a bacteriocin produced by *Lactobacillus* casei CRL 705", International Journal of Food Microbiology, Elsevier Science Publishers, Amsterdam, NL, vol. 29, No. 2-3, 1996, pp. 397-402.

Iowa State University Research Foundation, Inc., PCT/US2007/000298, International Search Report dated Apr. 9, 2008, 7 pages.

Walburger A. et al., "The Tol/Pal system function requires an interaction between the C-terminal domain of TolA and the N-terminal domain of TolB", Molecular Microbiology, vol. 44:3 pp. 695-708 (2002). XP002254022.

* cited by examiner

ANTIBIOTIC ALTERNATIVES

CROSS-REFERENCE TO RELATED APPLICATION

The present invention is a continuation-in-part of PCT/US05/08512 filed Mar. 15, 2005 which claims priority to U.S. Provisional Application Ser. No. 60/553,209 filed Mar. 15, 2004. The disclosures of these applications are specifically incorporated herein by reference.

BACKGROUND OF THE INVENTION

It is estimated that over 50% of all economic losses in weaned pigs are due to *Escherichia coli* infections, causing either diarrhea or edema disease. In addition to the *E. coli* strains responsible for disease in pigs, other *E. coli*, as well as *Salmonella*, strains also colonize the intestinal tract of pigs. Many of these strains are of major concern for human food safety. The U.S. Centers for Disease Control and Prevention (CDC) estimates that in the year 2000 over 1.4 million people suffered and more than 600 died, in this country, from food-borne disease caused by *Salmonella* and *E. coli* 0157:H7. The costs attributed to these diseases were approximately $3.1 billion.

The bacterial strains considered primarily responsible for *E. coli* infections in pigs, F4 (K88) and F18, are not well controlled by traditional prophylactic antibiotic treatments. With worldwide concerns over the use of prophylactic antibiotics in animal agriculture, the development of alternatives to conventional antibiotics is urgently needed to protect swine from these *E. coli* infections.

Probiotics have been explored as one alternative to the use of conventional antibiotics. A "probiotic" strategy is one that employs the use of microflora to reduce pathogenic bacteria (including food-borne pathogens) in the gut. Probiotic techniques involve the introduction of a healthy microbial population to the gastrointestinal (GI) tract, or providing a limiting nutrient, sometimes termed a "prebiotic", that allows an existing commensal microbial population to expand its role in the gastrointestinal tract. The addition of a non-pathogenic microbial culture to the intestinal tract of food animals in order to reduce colonization or decrease populations of pathogenic bacteria in the gastrointestinal tract is referred to as "competitive exclusion".

Competitive exclusion cultures may be composed of a single strain, several strains, or even several species of microorganisms. Depending on the stage of production, or more specifically, the maturity of the gut, the goal of this culture can be the exclusion of pathogens from the naïve gut of a neonatal animal, or the displacement of an already established pathogenic bacterial population.

Some bacteria produce antimicrobial protein compounds (traditional antibiotics, as well as bacteriocins, or colicins) in order to eliminate competitive bacteria, and have therefore shown additional promise for their use in competitive exclusion products. Protein antibiotics are attractive alternatives to conventional antibiotics used in animal feed, since they are not absorbed intact by the animal and, therefore, leave no antibiotic residues in the meat. Additionally, bacteriocins have the potential for very favorable regulatory status by the U.S. Food and Drug Administration. Nisin, a bacteriocin, is generally regarded as safe for use as a food additive for its antimicrobial properties. The possibility of an effective antibiotic alternative being regulated as a food additive, rather than as a new animal drug, is further incentive for bacteriocin research among the animal health/feed industries.

Colicins are classified as either pore-forming or nuclease colicins based on their mode of bacteriocidal activity, and are further categorized based on their mode of membrane integration in sensitive bacteria. Members of both classes have been shown effective against gram-negative bacteria of concern for animal health and human food safety, such as *E. coli* and *Salmonella* strains, and therefore hold promise for use as alternatives to conventional antibiotics in animal diets.

Colicins are a class of bacteriocins produced by, and effective against *E. coli* and closely related members of the family Enterobacteriaceae. Pore-forming colicins are between 387 and 626 amino acids in length, and provide their antibacterial effect by crossing the outer membrane, spanning the periplasm, and inserting into the bacterial inner cell membrane to form voltage-dependent ion channels. The ion leakage caused by these channels uncouples energy expenditures from growth, causing death in cellular targeted bacteria. Nuclease colicins kill sensitive cells by non-specific degradation of DNA or specific cleavage of rRNA.

Shiga toxin producing *E. coli* strains, such as 0157:H7, which present serious human food safety concerns, have also been shown to be sensitive to colicins. Doyle et al., U.S. Pat. No. 5,965,128, discloses the use of colicin producing *E. coli* as probiotics in cattle to reduce *E. coli* 0157:H7 shedding. Further, Lyon et al., U.S. Pat. No. 5,549,895, discloses the use of naturally produced colicins for inhibiting *E. coli* 0157:H7 and other *Escherichia* species, as well as *Shigella* species in food products, on carcasses, and on hard surfaces as a sanitizer.

Although colicins have shown potential as alternatives to conventional antibiotics in animal feed, it would not be cost effective to purify this protein from naturally occurring colicin producing *E. coli* strains, nor to include the levels of these bacteria necessary to obtain an antimicrobial effect in the feed.

It is therefore a primary objective of the present invention to produce alternatives to conventional antibiotics for use in the animal feed industry.

It is a further objective of the present invention to produce recombinant colicins in a yeast expression system.

It is a further objective of the present invention to produce recombinant colicins in a plasmid expression system.

It is still a further objective of the present invention to produce recombinant colicins that are effective against pathogenic bacteria.

It is yet a further objective of the present invention to produce recombinant colicins that may be used as a probiotic culture.

It is yet a further objective of the present invention to produce recombinant colicins that are effective against *E. coli* and *Salmonella* strains of importance to human food safety.

It is a further objective of the present invention to produce recombinant colicins that are effective against pathogenic bacteria that is cost effective.

The method and means of accomplishing each of the above objectives as well as others will become apparent from the detailed description of the invention which follows hereafter.

SUMMARY OF THE INVENTION

The present invention provides a method for the production of colicins from a recombinant organism whereby a suitable host organism is transformed with a transformation cassette comprising a gene encoding a pore-forming or nuclease colicin. The transformed host organism is then cultured under suitable conditions, and the colicins recovered and purified.

The invention further provides transformed hosts comprising expression cassettes capable of expressing colicins.

The suitable host organism used in the method is bacteria or yeast. The suitable host organism is more particularly selected from the group of genera consisting of *Citrobacter, Enterobacter, Klebsiella, Aerobacter, Lactobacillus, Aspergillus, Saccharomyces, Schizosaccharomyces, Pichia, Candida, Hansenula, Methylobacter, Escherichia, Salmonella, Bacillus, Streptomyces* and *Pseudomonas*.

The invention is also embodied in a transformed host cell comprising a gene encoding for a colicin, and a host cell transformed with the gene, whereby the transformed host produces colicin, whereby the host cell is preferably *P. pastoris* or *E. coli*. The colicins of this invention have bactericidal activity against various strains of organisms that are of concern in animal health and food safety, including strains of *E. coli* and *Salmonella*. It has also been surprisingly found that the colicins have activity against strains of *Listeria*.

DETAILED DESCRIPTION OF THE DRAWINGS

DETAILED DESCRIPTION OF THE PREFERRED EMBODIMENT

Figure 1:
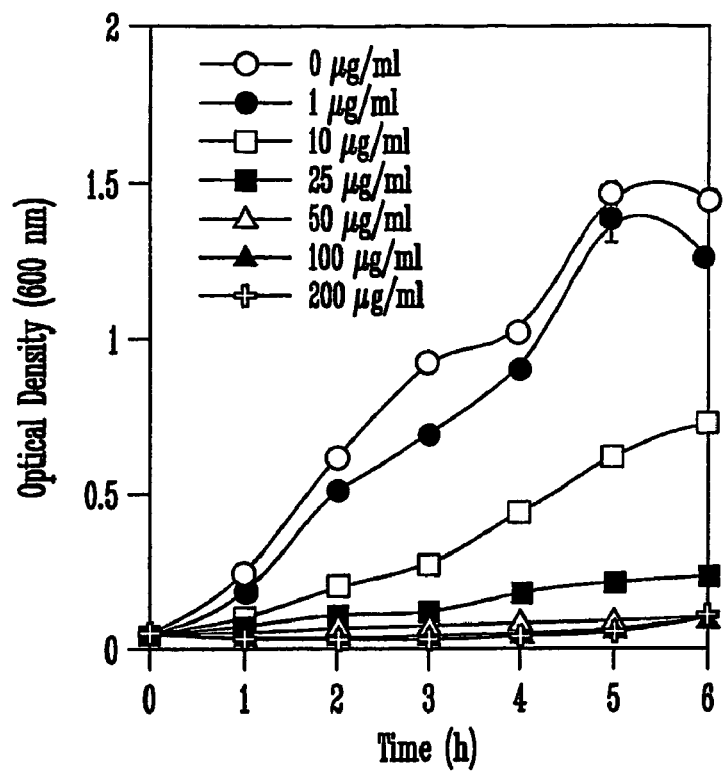
FIG. 1 illustrates the effect of Colicin E1 on the growth of *Escherichia coli* F4 (K88).

The present invention provides a method for biological production of colicins in a recombinant organism. The method incorporates a microorganism containing a gene coding for a pore-forming colicin, such as colicins, A, B, E1, Ia, and N (Morlon et al., 1983; Mankovich et al., 1986; Pugsley, 1987), or a nuclease colicin, such as E2, E8, E9, E7, E5, E4, DF13, E6, or E3. Such colicins are easily isolated from non-pathogenic strains of *E. coli* using methods well known in the art. In comparison to conventional antibiotic prophylactic therapy, the present method provides a relatively inexpensive and environmentally responsible means of protecting swine and other animals from *E. coli* infections. Two pore-forming colicins in particular, namely E1 and N, have been demonstrated to be especially effective against the F 18 and F4 strains of *E. coli*, respectively. Colicin E1 has also been shown to have extensive activity against *L. monocytogenes*. The colicins are produced as described above and purified using conventional methods, such as affinity chromatography.

The following definitions are to be used to interpret the claims and specification.

The terms "host cell" or "host organism" refer to a microorganism capable of receiving foreign or heterologous genes and of expressing those genes to produce an active gene product. The terms "organism(s)" and "microorganism(s)" shall be used interchangeably and will refer to prokaryotic and eukaryotic organisms that exist in nature as single cells, where each cell is capable of sustaining life independently of other cells of the same type.

The terms "foreign gene", "foreign DNA", "heterologous gene" and "heterologous DNA" refer to genetic material native to one organism that has been placed within a host organism by various means.

The terms "recombinant organism" and "transformed host" refer to any organism having been transformed with heterologous or foreign genes. The recombinant organisms of the present invention express foreign genes encoding pore-forming or nuclease colicins.

"Gene" refers to a nucleic acid fragment that expresses a specific protein, including regulatory sequences preceding (5' non-coding) and following (3' non-coding) the coding region. The terms "native" and "wild-type" refer to a gene as found in nature with its own regulatory sequences.

The terms "encoding" and "coding" refer to the process by which a gene, through the mechanisms of transcription and translation, produces an amino acid sequence. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. In some cases, it may in fact be desirable to make mutants of the sequence in order to study the effect of alteration on the biological activity of the protein. Each of the proposed modifications is well within the routine skill in the art, as is determination of retention of biological activity in the encoded products.

The term "expression" refers to the transcription and translation to gene product from a gene coding for the sequence of the gene product.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the product of a transformation.

The term "genetically altered" refers to the process of changing hereditary material by transformation or mutation.

Recombinant organisms containing the necessary genes that will encode colicins in accordance with this invention may be constructed using techniques well known in the art. In the present invention, genes encoding colicins A, B, E1, Ia, and N were isolated in the laboratory from nonpathogenic strains of *E. coli* obtained from the National Collection of Type Cultures (NCTC, London, UK) and used to transform host strains, such as *E. coli* DH5α, ECL707, AA200, JM109, or W1485; *Saccharomyces cerevisiae; Lactobacillus; P. pastoris* or the *Klebsiella* pneumoniae strains ATCC 25955 or ECL 2106.

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of DNA suitable for transformation using appropriate vectors.

Genes encoding colicins are well known in the art, as are their sources. See e.g. Pugsley and Oudega, 1987 and Giilor et al., 2004. it is contemplated that any gene encoding a pore-forming or nuclease colicin or having pore-forming or nuclease colicin-like activity is suitable for the purposes of the present invention, wherein that activity is capable of forming ion channels in the plasma membrane of bacteria, resulting in membrane depolarization, or capable of non-specific degradation of DNA or specific cleavage of rRNA in sensitive cells.

Suitable host cells for the recombinant production of colicin may be either prokaryotic or eukaryotic (yeast). Preferred hosts include *Citrobacter, Enterobacter, Klebsiella, Aerobacter, Lactobacillus, Aspergillus, Saccharomyces, Schizosaccharomyces, Pichia, Candida, Hansenula, Methylobacter, Escherichia, Salmonella, Bacillus, Streptomyces* and *Pseudomonas*. Most preferred in the present invention are *Pichia* and *Escherichia* species, with *P. pastoris* and *E. coli* being most preferred for cost reasons.

The present invention provides a variety of vectors and transformation and expression cassettes suitable for the cloning, transformation and expression of colicins into a suitable host cell. Suitable vectors can be derived, for example, from a bacteria or a yeast. Protocols for obtaining and using such vectors are known to those in the art. (Sambrook et al., Molecular Cloning: A Laboratory Manual—volumes 1,2,3 (Cold Spring Harbor Laboratory, Cold Spring Harbor, N.Y., (1989)).

Suitable bacterial vectors for use in the invention are those that can be replicated in the host cells listed above. For example, in a preferred embodiment of the invention, constitutive expression of an *E. coli* colA gene is accomplished in *Lactobacillus* by placing this gene downstream of a strong *Lactobacilli* promoter sequence (Djordjevic et al., 1997). This plasmid and promoter sequence combination has been used successfully to express an *E. coli* gusA gene in *L. gasseri* (Russell and Klaenhammer, 2001).

In a preferred embodiment using a yeast system, expression of an *E. coli* colA gene is placed in correct reading frame behind the alpha-factor signal peptide of *Sacchromyces cerevisiae*. This signal peptide has been shown to direct efficient secretion of recombinant *E. coli* proteins in yeast systems (Brake et al., 1984; Rodriguez et al., 1999; Stahl, 2001). In this embodiment, expression is preferably controlled by the glyceraldehyde-3-phosphate dehydrogenase promoter or alcohol oxidase I promoter, from a methylotropic yeast, *Pichia pastoris*. These promoters direct constitutive or inducible expression, respectively, of the gene of interest.

Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell although it is to be understood that such control regions need not be derived from the genes native to the specific species chosen as a production host. Examples of suitable vectors for use in the invention include Pgemt-Easy (*E. coli* T vector for subcloning PCR products); pGAPz (an integrative *P. pastoris* expression vector, also an *E. coli* shuttle vector; pGAPzα (an integrative *P. pastoris* expression vector, also an *E. coli* shuttle vector); pPICZα (an integrative *P. pastoris* expression vector, also an *E. coli* shuttle vector); pPICZ (an integrative *P. pastoris* expression vector, also an *E. coli* shuttle vector), and pTRK664 (*Lactobacillus* expression vector, and an *E. coli* shuttle vector).

Initiation control regions or promoters, which are useful to drive expression of the colicin encoding genes in the desired host cell, are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); *Lactococcus lactis* lacA and *Lactobacillus acidophilus* ATCC 4356 (useful for expression in *Lactobacilli*); slpA AOX1 (useful for expression in *Pichia*); and lac, trp, $\lambda P_L$, $\lambda P_R$, T7, tac, and trc (useful for expression in *E. coli*). Termination control regions may also be derived from various genes native to the preferred hosts.

Once suitable cassettes are constructed they are used to transform appropriate host cells. Introduction of the cassette containing the genes encoding the colicins, either separately or together into the host cell may be accomplished by known procedures such as by transformation (e.g., using calcium-permeabilized cells, electroporation) or by transfection using a recombinant phage virus. (Sambrook et al., supra.)

Fermentation media in the present invention must contain suitable carbon substrates. Suitable substrates may include, but are not limited to, monosaccharides such as glucose and fructose, oligosaccharides such as lactose or sucrose, polysaccharides such as starch or cellulose, or mixtures thereof, and unpurified mixtures from renewable feedstocks such as cheese whey permeate, cornsteep liquor, sugar beet molasses, and barley malt. Additionally, the carbon substrate may also be one-carbon substrates such as carbon dioxide, or methanol for which metabolic conversion into key biochemical intermediates has been demonstrated.

In addition to utilization of one and two carbon substrates, methylotrophic organisms are also known to utilize a number of other carbon-containing compounds such as methylamine, glucosamine and a variety of amino acids for metabolic activity. For example, methylotrophic yeast are known to utilize the carbon from methylamine to form trehalose or glycerol (Bellion et al., Microb. Growth C1 Compd., [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., Arch. Microbiol., 153(5), 485-9 (1990)). Hence, the source of carbon utilized in the present invention may encompass a wide variety of carbon-containing substrates and will only be limited by the requirements of the host organism.

Although it is contemplated that all of the above mentioned carbon substrates and mixtures thereof are suitable in the present invention, preferred carbon substrates are monosaccharides, oligosaccharides, polysaccharides, and one-carbon substrates. More preferred are sugars such as glucose, fructose, glycerol, sucrose and single carbon substrates such as methanol and carbon dioxide.

In addition to an appropriate carbon source, fermentation media must contain suitable minerals, salts, cofactors, buffers and other components, known to those skilled in the art, suitable for the growth of the cultures and promotion of the enzymatic pathway necessary for glycerol production.

Typically, cells are grown at 28-40° C. in appropriate media. Preferred growth media in the present invention are common commercially prepared media such as Luria Bertani (LB) broth, Sabouraud Dextrose (SD) broth, MS broth, Yeast Peptone Dextrose, BMMY, GMMY, or Yeast Malt Extract (YM) broth. Other defined or synthetic growth media may also be used and the appropriate medium for growth of the particular microorganism will be known by someone skilled in the art of microbiology or fermentation science.

Suitable pH ranges for the fermentation are between pH 4.0 to pH 9.0. Reactions may be performed under aerobic or anaerobic conditions. The present invention may be practiced using either batch, fed-batch or continuous processes and that any known mode of fermentation would be suitable.

Methods for the purification of proteins and polypeptides from fermentation media are known in the art. For example, polypeptides can be obtained from cell media by subjecting the reaction mixture to extraction with an organic solvent, distillation, ultrafiltration, and ion exchange chromatography, and column chromatography. The recombinant colicins of this invention may be identified directly by submitting the media to functional assay or high pressure liquid chromatography (HPLC) analysis. The levels of expression of the colicin proteins are measured by bacterial inhibition assays and other methods well known in the art.

The following examples are offered to illustrate but not limit the invention. Thus, they are presented with the understanding that various modifications may be made and still be within the spirit of the invention.

EXAMPLE 1

Colicin Production, Purification, and Efficacy

Colicin Production and Purification

Colicin producing *E. coli* strains, obtained from the National Collection of Type Cultures (Public Health Laboratory Service, London, England), were inoculated into Luria Broth (LB) to a starting $OD_{600}$~0.1, and incubated with shaking at 37° C. When the cultures reached an $OD_{600}$=0.9 colicin production was induced by the addition of 0.2 U Mitomycin C (Sigma)/mL culture. The cell free supernatant was obtained by centrifugation 5.5 h later, and concentrated by ultrafiltration in a stir-cell apparatus (Amicon, Millipore, Bedford, Mass.) across a regenerated cellulose membrane with a 30 kDa cut-off (Millipore). The concentrated sample was then desalted against 10 mM Tris-Cl, pH 8 and purified by ion exchange chromatography. The desalted samples were applied to a column containing Q Sepharose (Amersham Biosciences, Piscataway N.J.), equilibrated with 10 mM Tris-Cl, pH 8.0 (equilibration buffer), and exhaustively washed with the equilibration buffer. The bound protein was eluted with a continuous NaCl gradient using an AKTAprime chromatography system (Amersham Bioscience). The fractions containing the highest concentrations of colicin, determined by SDS-PAGE followed by Coomasie Blue staining, were pooled and concentrated by ultrafiltration. The protein concentrations of these samples were determined in each pooled sample (Lowry et al., 1951), and the percentage colicin was determined by densitometry using a 16 bit mexapixel CCD camera, FluorChem 8800, and FluorChem IS800 software (Alpha Innotech, San Leandro, Calif.).

Inhibition of Growth Assays

Pure cultures of *E. coli* F4 (K88) and F18 were obtained from the culture collection at the USDA-ARS Federal Food Safety Research Unit (College Station, Tex.). These cultures were grown overnight in LB at 37° C. with shaking, and then used to inoculate a flask of LB to an $OD_{600}$~0.05. The freshly inoculated LB was then aliquoted (5 mL) into culture tubes containing various colicin doses. The volume of the colicin doses was made constant by the addition of 10 mM Tris, pH 8. The total volume of each dose, including the 0 μg/mL colicin control, was 175 μL. These tubes were then incubated with shaking at 37° C., and their $OD_{600}$ determined hourly for six hours. Quantitative determination of the colony forming units (CFU) of the *E. coli* strains were obtained by serial dilutions and direct plating on LB, initially and 3 h post-inoculation. There experiments were repeated in triplicate, and the values presented are means.

Results

Production and Purification of Colicins

Yields of 1.1 mg of purified Colicin N/L of culture and 7.6 mg of purified Colicin E1/L of culture were obtained with the aforementioned production and purification strategy. The purity of the Colicin N and E1 isolates were 30% and 85%, respectively, as determined by densitometry.

Efficacy of Colicin E1 against *Escherichia coli* F4 (K88) and F18

Figure 2:
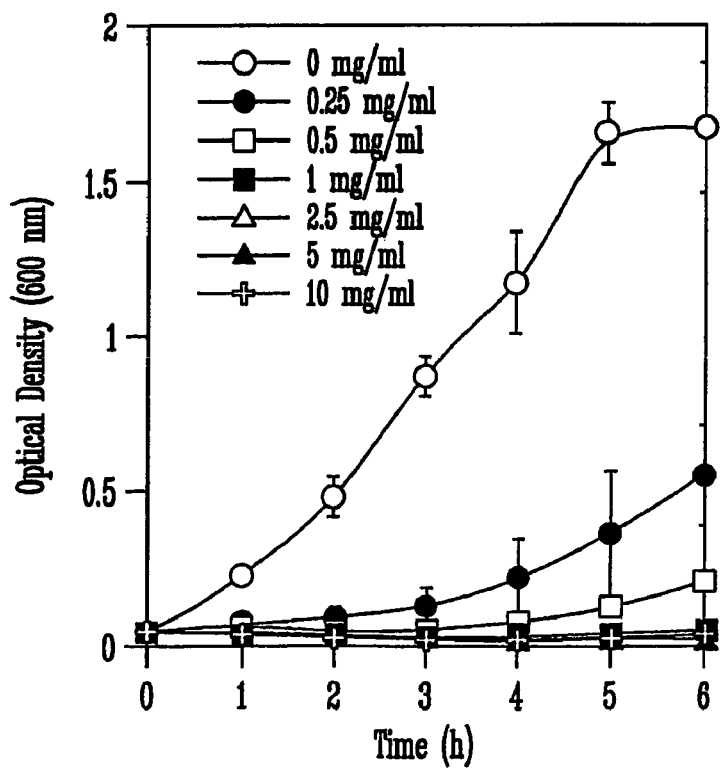
FIG. 2 illustrates the effect of Colicin E1 on the growth of *Escherichia coli* F18.

Colicin E1 significantly reduced the growth rate of *E. coli* F4 (K88) with 10 μg/mL of culture (FIG. 1). A dose of 50 μg/mL was needed to inhibit all growth of F4 (K88) for 6 hours. A significant reduction in the growth of F18 was seen with as little as 0.25 μg Colicin E1/mL of culture, and a complete inhibition of growth for 6 hours was seen with 1 μg/mL of culture (FIG. 2). Colicin E1 showed bactericidal activity against both *E. coli* F4 (K88) and F18. After 3 hours of incubation with 50 μg of Colicin E1/mL of media, there was approximately one log less F4 (K88) CFU/mL than in the initial inoculum (Table 1). This dose caused an approximately three log difference in F4 (K88) CFU/mL between the treated and untreated cultures. These same trends were also seen when F18 was incubated with only 1 μg of Colicin E1/mL of media. A dose of 100 μg of Colicin E1/mL caused a greater decline in *E. coli* F18 CFU/mL., but did not eliminate viable cells after three hours of incubation.

TABLE 1

Effect of Colicins on the Viability of *Escherichia coli* F4 (K88) and F18 After 3 Hours Incubation
Initial CFU/mL were $6 \times 10^7$ and $1 \times 10^7$ for *E. coli* F4 (K88) and F18, respectively.

| *E. coli* | Colicin E1 Dose, μg/mL | CFU/mL | Colicin N Dose, μg/mL | CFU/mL |
|---|---|---|---|---|
| F4 (K88) | 0 | $3 \times 10^9$ | 0 | $3 \times 10^9$ |
|  | 50 | $5 \times 10^6$ | 10 | $1.1 \times 10^7$ |
|  | 200 | $4 \times 10^6$ | 50 | $6 \times 10^5$ |
| F18 | 0 | $2 \times 10^9$ | 0 | $2 \times 10^9$ |
|  | 1 | $1.2 \times 10^6$ | 50 | $1 \times 10^6$ |
|  | 100 | $5 \times 10^4$ | 100 | $4 \times 10^5$ |

Efficacy of Colicin N Against *E. coli* F4 (K88) and F18

Figure 3:
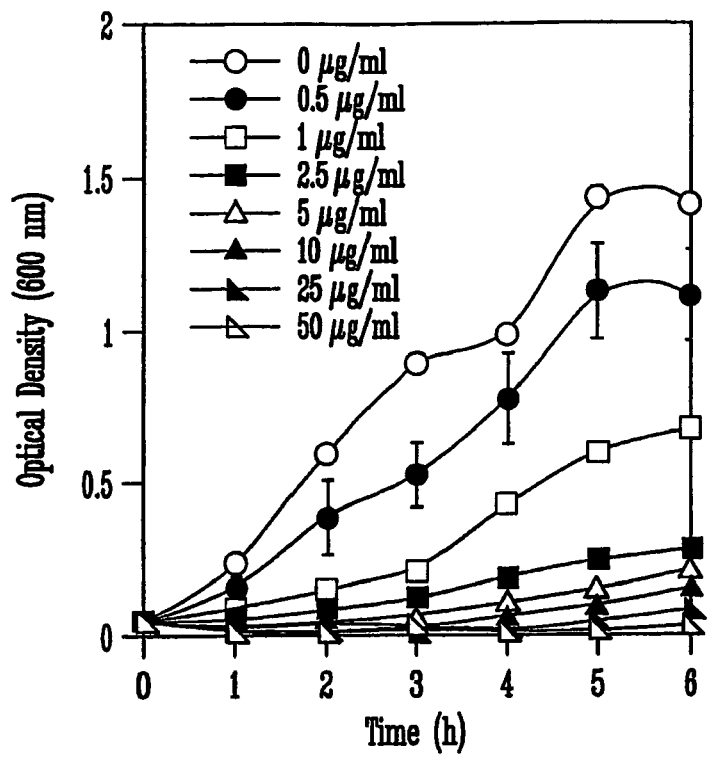
FIG. 3 illustrates the effect of Colicin N on the growth of *Escherichia coli* F4 (K88).
Figure 4:
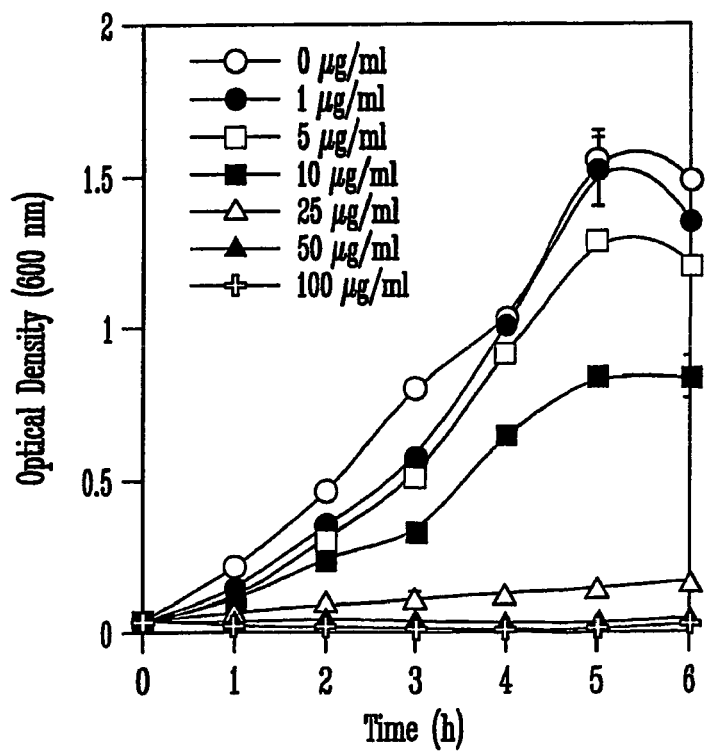
FIG. 4 illustrates the effect of Colicin N on the growth of *Escherichia coli* F18.

Colicin N was effective in inhibiting the growth of *E. coli* F4 (K88) and F18 at doses of 1 and 10 μg/mL of culture, respectively. (FIGS. 3 and 4). To completely inhibit the growth of these strains for 6 hours required 25 μg of Colicin N/mL of F4 (K88) and 50 μg/mL of F18 (FIGS. 3 and 4). A 10 μg of Colicin N/mL of F4 (K88) dose did not allow any increase over the initial inoculum in the number of CFU/mL after 3 hours of incubation (Table 1). With this dose there was greater than a 3 log reduction in the F4 (K88) CFU/mL after 3 hours incubation, when compared to the control. After 3 hours of incubation with 50 μg of Colicin N/mL of media, there was approximately one log less F18 CFU/mL than in the initial inoculum (Table 1), and greater than three log less F18 CFU/mL than compared to the untreated culture after 3 hours incubation.

Discussion

Both of the *E. coli* strains considered primarily responsible for post-weaning diarrhea and edema disease in swine were sensitive to Colicin E1 and Colicin N. While both colicins inhibit the growth of these strains, their efficacy varied substantially. Colicin N was dramatically more effective than Colicin E1 against *E. coli* F4 (K88). Significant reductions in growth of *E. coli* F4 (K88) were seen with 10 fold less Colicin N than Colicin E1 (FIGS. 1 and 2). With equal dosage (50 μg/mL), approximately 1 log fewer CFU/mL were seen with Colicin N than with Colicin E1, after three hours of incubation (Table 1). Colicin N was also more effective in reducing the growth of F4 (K88) than F18 (FIGS. 3 and 4). To completely inhibit the growth of F18 required approximately 10 fold more Colicin N than was needed for F4 (K88). The effectiveness of Colicin E1 against these *E. coli* strains was opposite that of Colicin N.

Colicin E1 was more effective against F18 than against F4 (K88), requiring approximately 50 fold less to completely inhibit the growth of F18 (FIGS. 1 and 2). Colicin E1 was highly effective against F18 with as little as 0.25 μg/mL dramatically inhibiting its growth. Complete inhibition of growth, for six hours, was obtained with only 1 μg/mL, while greater than 25 μg Colicin N/mL was required for the complete inhibition of growth. Although growth was completely inhibited at this dosage, even a 100 fold increase in Colicin D1 could not eliminate all of the viable F18 in culture. Approximately $5 \times 10^4$ CFU/mL remained after 3 hours of incubation with 100 μg of Colicin E1/mL (original inoculum was $1 \times 10^7$ CFU/mL).

EXAMPLE 2

Inhibition of Growth of *Escherichia coli* 0157:H7 In Vitro

Materials and Methods

Colicin Production and Purification

Each colicin was produced from a specific colicin-producing *E. coli* K-12 strain (NC50129-01 containing plasmid pCo1A-CA31, NC50132-01 containing plasmid pColE1-K53, and NC50145-01 containing plasmid pColN-284) obtained from the National Collection of Type Cultures (Public Health Laboratory Service, London, UK). Cultures were inoculated into Luria-Bertani (LB) broth to an initial optical density of 600 mn ($OD_{600}$) of approximately 0.1 and incubated in a shaker at 37° C. When the cultures reached OD600=0.9, colicin production was induced by the addition of 0.2 U of mitomycin C per ml of culture (Sigma Chemicals, St. Louis, Mo.). The cell-free supernatant was obtained by centrifugation 5.5 h later and concentrated by ultrafiltration in a stir-cell apparatus (Amicon, Millipore, Bedford, Mass.) across a regenerated cellulose membrane with a 30-kDa cut-off (Millipore). The concentrated sample was then desalted against 10 mM Tris-Cl, pH 8, and purified by ion exchange chromatography. The desalted samples were applied to a column containing Q Sepharose (Amersham Biosciences, Piscataway N.J.), equilibrated with 10 mM Tris-Cl, pH 8.0 (equilibration buffer), and exhaustively washed with the equilibration buffer. The bound protein was eluted with a continuous NaCl gradient on an AKTAprime chromatography system (Amersham Bioscience). The fractions containing the highest concentrations of colicin, determined by sodium dodecyl sulfate-polyacrylamide gel electrophoresis followed by Coomasie blue staining, were pooled and concentrated by ultrafiltration. The protein concentrations of these samples were determined in each pooled sample (20), and percent colicin was determined by densitometry with the use of a 16-bit megapixel charge-coupled device camera (FluorChem 8800, Alpha Innotech, San Leandro, Calif.) and Fluor Chem IS800 software (Alpha Innotech).

Bacterial Strains and Culture Conditions

E. coli O157:H7 strains 933 (ATCC 43895) and 86-24 were obtained from the Food and Feed Safety Research Unit culture collection (U.S. Department of Agriculture/Agricultural Research Service, College Station, Tex.); both strains were originally isolated from human hemorrhagic colitis outbreaks. E. coli O157:H7 strain 933 was naturally resistant to 25 μg/ml novobiocin and were made resistant to 20 μg/ml nalidixic acid by repeated transfer and selection. E. coli O157:H7 86-24 was made resistant to streptomycin (100 μg/ml) by repeated transfer and selection. Differences in growth rates and antibiotic resistance profiles (other than for specifically selected and closely related antibiotics) were not detected between these antibiotic-resistant strains and wild-type parental strains (data not shown).

*Escherichia coli* O157:H7 strains 933 (ATCC 43895) and 86-24 were anaerobically (90% $N_2$, 5% $H_2$, 5% $CO_2$ atmosphere) incubated at 39° C. in anoxic tryptic soy broth (Difco Laboratories, Detroit, Mich.) to ensure colicin activity under anaerobic conditions similar to those within the gastrointestinal tract. Growth rates (n=2) were estimated via measurement of absorbance changes with a Spectronic 20D spectrophotometer (600 nm, Thermo Spectronic Inc., Madison, Wis.); growth rate was calculated with the formula (ln $OD_2$—ln $OD_1$)/ΔT. Final optical densities after 24 h of incubation were measured with a Gilford 2600 spectrophotometer (600 nm, 1-cm cuvette). Cultures with optical densities greater than 0.7 OD units were appropriately diluted in 0.9% NaCl.

Quantitative Bacterial Enumeration

Samples were taken from incubations at 6 and 24 h to determine the effect of colicins on populations of E. coli O157:H7. Samples were serially diluted (in 10-fold increments) in phosphate-buffered saline (pH 7.0) and subsequently plated on MacConkey's agar (supplemented with 25 μg/ml novobiocin and 20 μg/ml nalidixic acid for E. coli O157:H7 strain 933 or with 100 μg/ml streptomycin for E. coli O157:H7 strain 86-24) and incubated at 37° C. overnight for direct counting (CFU per milliliter).

Colicin Addition

To initially evaluate the effectiveness of these colicins against E. coli O157:H7 strains, cultures were inoculated into tryptic soy broth tubes containing equivalent concentrations (4.1 μg/ml) of each of the individual colicins tested (A, E1, and N). To determine the effective range of doses for use in more complex mixed culture and in vivo studies, freshly inoculated tryptic soy broth was added (5 ml) to culture tubes containing concentrations (0 to 40.8 μg of each colicin per ml) of colicin A, colicin E1, and colicin N. The total volume of each colicin addition, including the 0 μg/ml colicin control, was 175 μl; the volume of the colicin dose was made constant by the addition of sterile, anoxic 10 mM Tris, pH 8. To determine the lowest effective dose of colicin E1 against both E. coli O157:H7 strains, cultures were grown in the presence of 0, 0.016, 0.032, 0.064, 0.128, 0.255, 0.51, 1.02, 2.04, 4.1, 7.7, 15.4, 28.8, and 40.8 μg of colicin E1 per ml.

Statistical Analysis

Experiments were performed in duplicate, and the values presented are means. Students' t test was used to determine significance of differences between means.

Chemicals

Unless specifically mentioned, all chemicals were obtained from Sigma Chemical Company.

Results

Effect of Colicins on E. coli O157:H7

Figure 5:
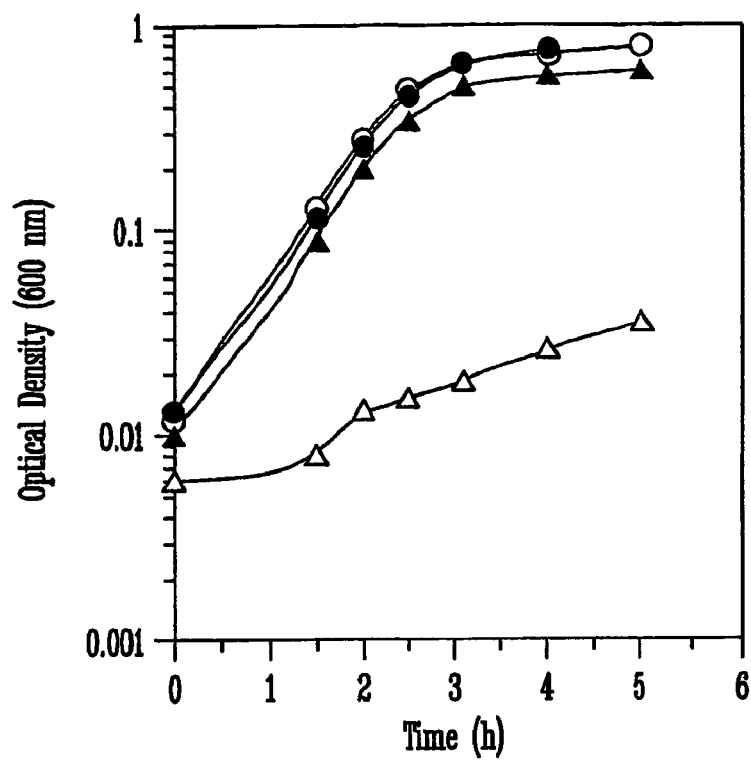
FIG. 5 illustrates the effect of colicins A, N, and E1 (4.1 µg/ml for each individual colicin) on increase in optical density (600 nm) of *E. coli* 057:H7 strain 933. O, control; ●, colicin A-treated; Δ, colicin E1-treated; and ▲, colicin N-treated cultures.
Figure 6:
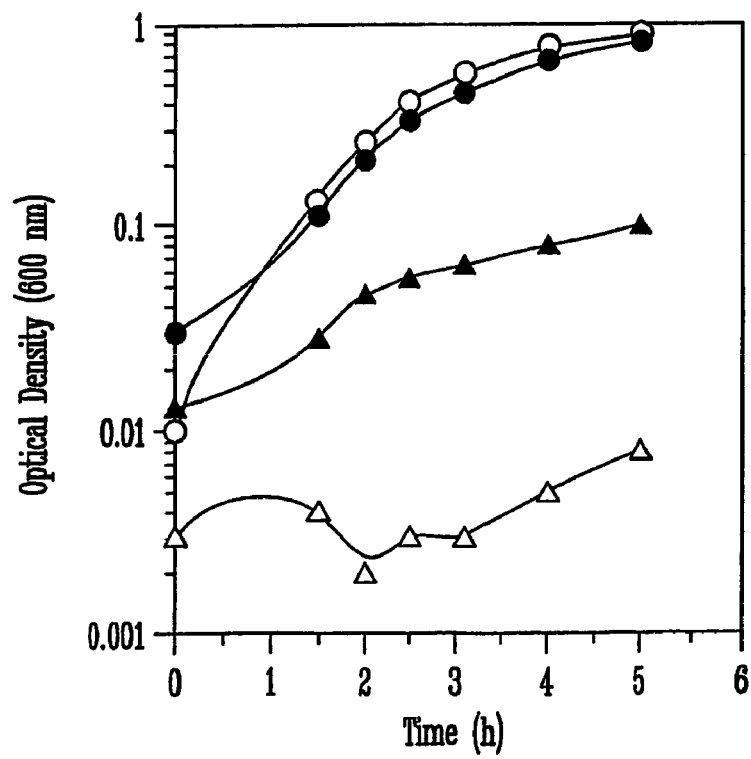
FIG. 6 illustrates the effect of colicins A, N, and E1 (4.1 µg/ml for each individual colicin) on increase in optical density (600 nm) of *E. coli* 057:H7 strain 86-24. O, control; ●, colicin A-treated; Δ, colicin E1-treated; and ▲, colicin N-treated cultures.
Figure 7:
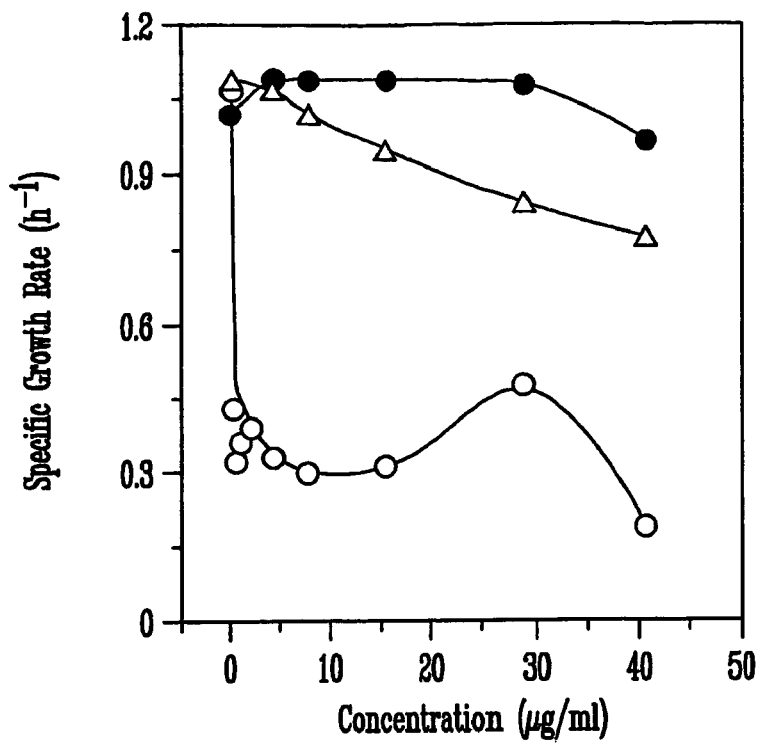
FIG. 7 illustrates the effect of colicins A, N, and E1 on the maximal specific growth rates ($h^{-1}$) of *E. coli* 057:H7 strain 933. Δ, colicin A-treated; O, colicin E1-treated; and ●, colicin N-treated cultures.
Figure 8:
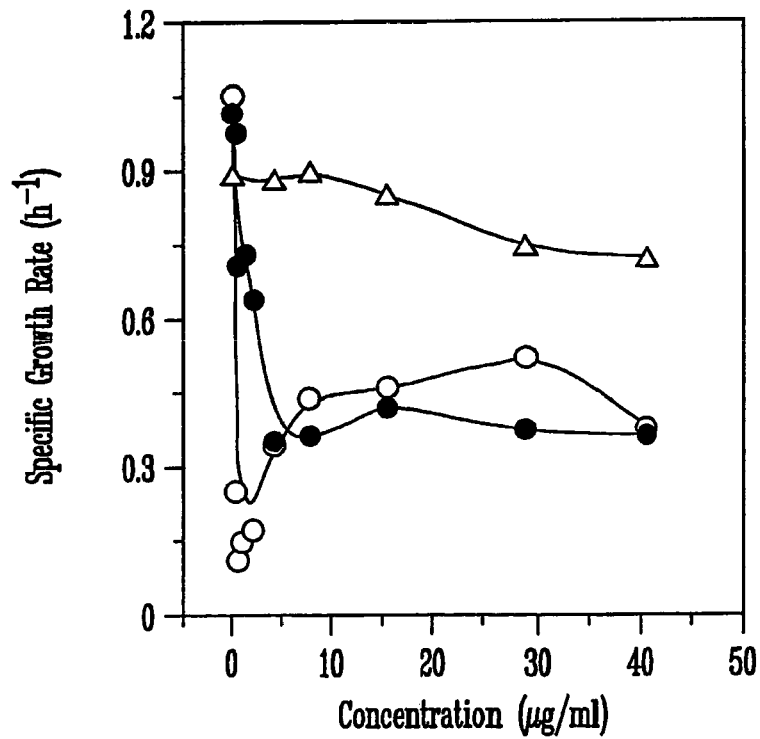
FIG. 8 illustrates the effect of colicins A, N, and E1 on the maximal specific growth rates ($h^{-1}$) of *E. coli* 057:H7 strain 86-24. Δ, colicin A-treated; O, colicin E1-treated; and ●, colicin N-treated cultures.

E. coli O157:H7 grew rapidly in tryptic soy broth, but the addition of colicins affected growth (FIGS. 5 and 6). Colicin E1 significantly ($P<0.05$) reduced growth of both E. coli O157:H7 strains 933 and 86-24 (FIGS. 5 and 6). Colicin N did not affect the growth rate of E. coli O157:H7 strain 933 (FIG. 5) but did reduce the OD or growth rate of E. coli O157:H7 strain 86-24 (FIG. 6). Colicin A did not affect the OD of either strain of E. coli O157:H7. Colicin E1 significantly ($P<0.05$) reduced the specific growth rate of both strains of E. coli O157:H7 examined at low concentrations (FIGS. 7 and 8). Colicin N was nearly as effective as E1 against strain 86-24 but was not ($P>0.10$) effective against strain 933.

Regardless of the colicin dose used, all E. coli O157:H7 cultures eventually grew overnight,; therefore, final (24 h) optical densities were not significantly reduced in either strain by any of the colicins (data not shown).

Figure 9:
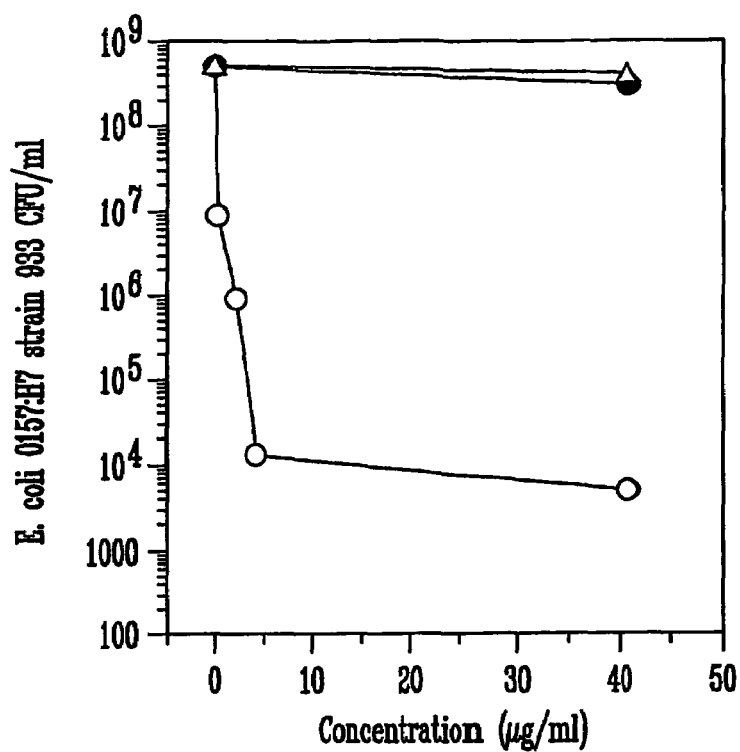
FIG. 9 illustrates the effect of colicins A, N, and E1 on bacterial populations (CFU/ml) of *E. coli* 057:H7 strain 933 after 6 h of incubation. Δ, colicin A-treated; O, colicin E1-treated; and ●, colicin N-treated cultures.
Figure 10:
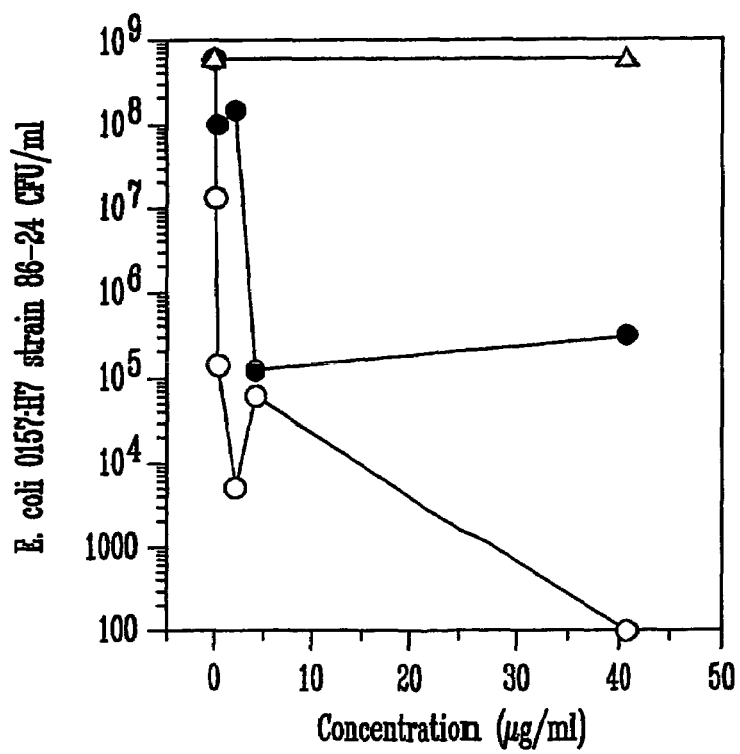
FIG. 10 illustrates the effect of colicins A, N, and E1 on bacterial populations (CFU/ml) of *E. coli* 057:H7 strain 86-24 after 6 h of incubation. Δ, colicin A-treated; O, colicin E1-treated; and ●, colicin N-treated cultures.
Figure 11:
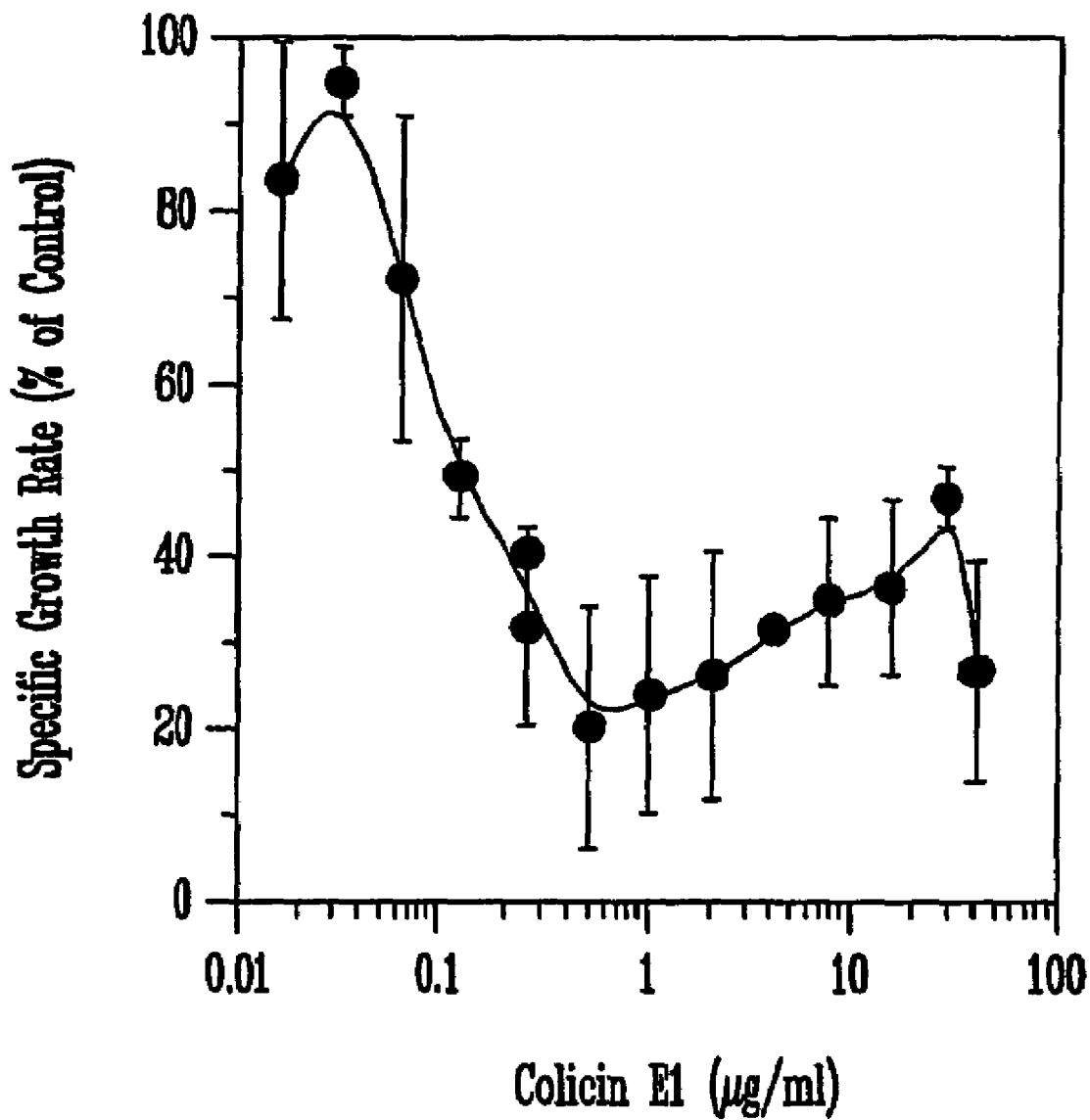
FIG. 11 illustrates the lowest colicin E1 concentrations (µg/ml) on the maximal specific growth rate ($h^{-1}$) of *E. coli* 0157:H7 strains. Error bars indicate standard deviations.
Figure 12:
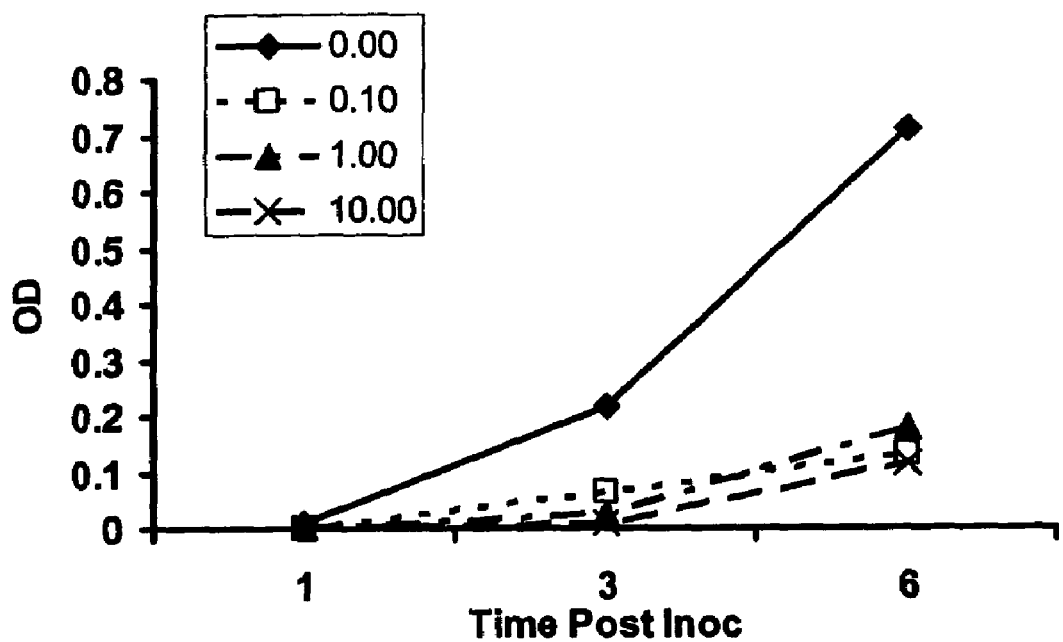
FIG. 12 illustrates the effect of Colicin E1 on the growth of *Listeria monocytogenes* strain FSIS 1126.
Figure 13:
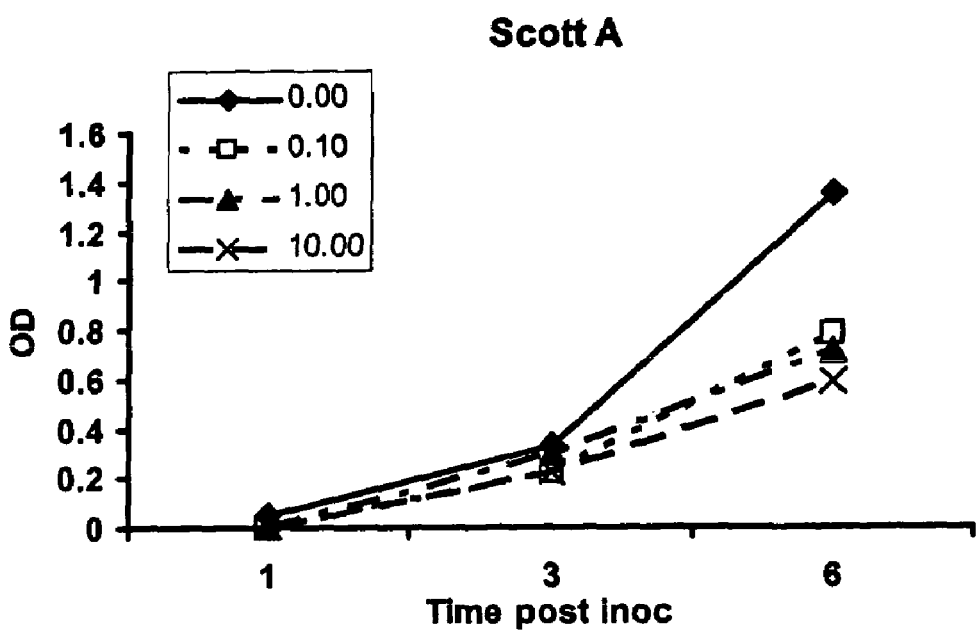
FIG. 13 illustrates the effect of Colicin E1 on the growth of *Listeria monocytogenes* strain Scott A.
Figure 14:
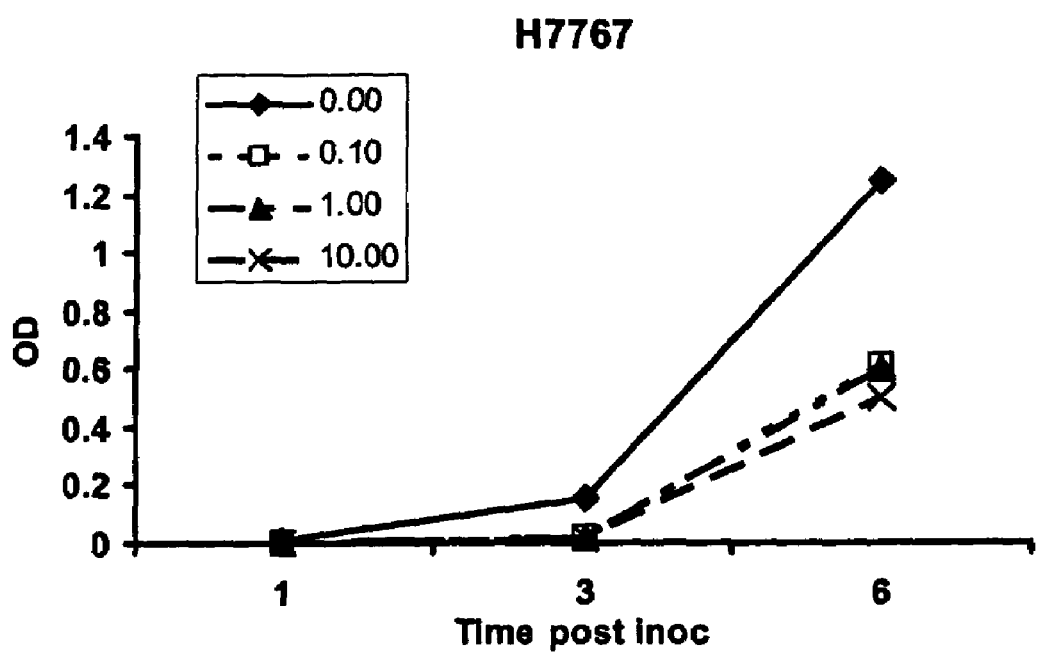
FIG. 14 illustrates the effect of Colicin E1 on the growth of *Listeria monocytogenes* strain H7767.
Figure 15:
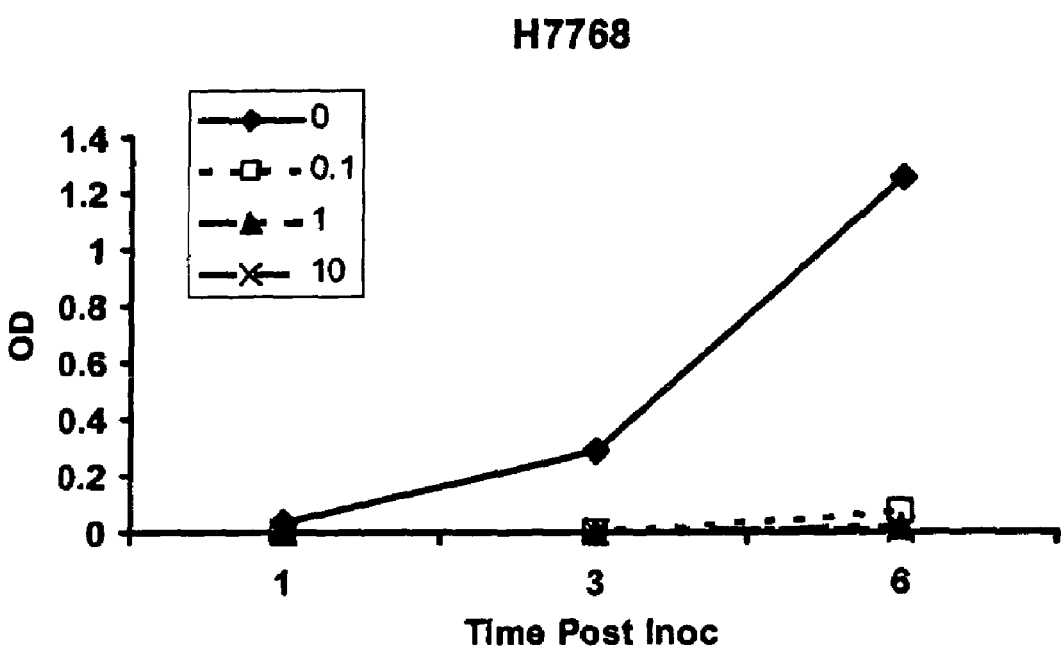
FIG. 15 illustrates the effect of Colicin E1 on the growth of *Listeria monocytogenes* strain H7768.
Figure 16:
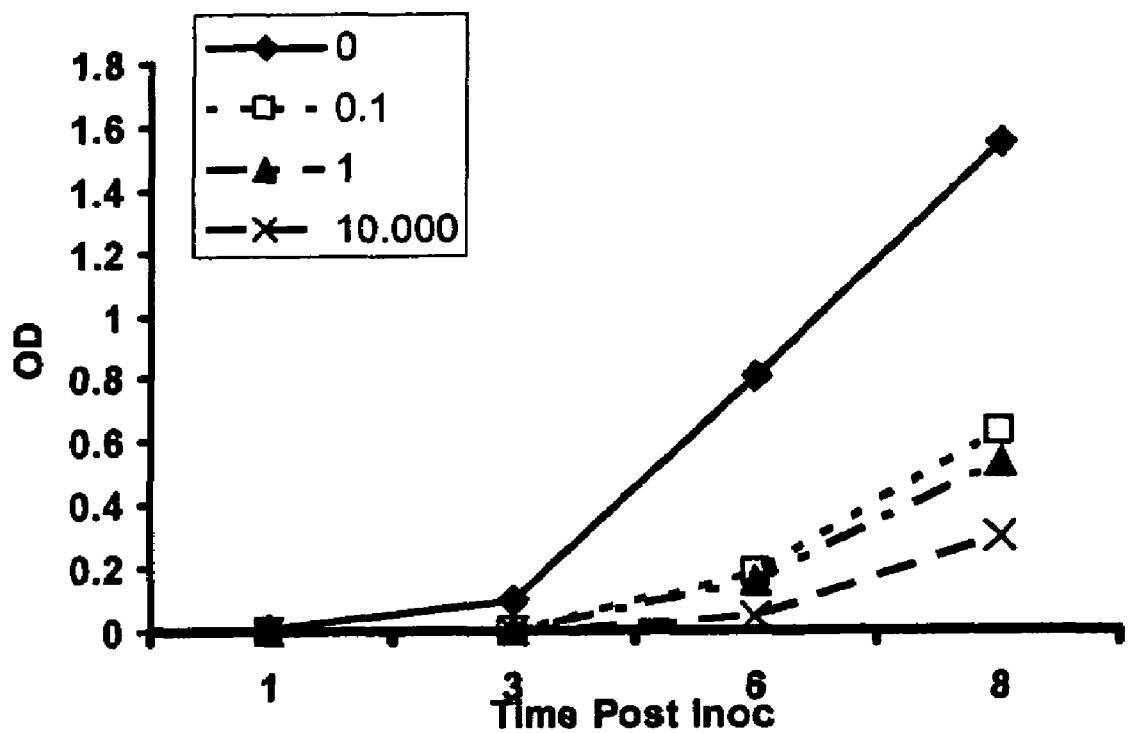
FIG. 16 illustrates the effect of Colicin E1 on the growth of *Listeria monocytogenes* strain H7769.

Bacterial populations of both E. coli O157:H7 strains were unaffected by colicin A (FIGS. 9 and 10). Treatment with colicin E1 significantly ($P<0.05$) reduced E. coli O157:H7 populations by at least 4 log units for both strains tested, whereas colicin N significantly ($P<0.05$) reduced populations only for E. coli O157:H7 strain 85-24 (FIG. 10). Because of the sensitivity of both strains of E. coli O157:H7 to colicin E1, the efficacy of very low doses against these strains was examined. Colicin E1 reduced ($P<0.05$) the specific growth rate of both strains of E. coli O157:H7 at concentrations below 0.1 μg/ml. (FIG. 11). In a negative control, *Salmonella Typhimurium* culture growth rates, final OD, and populations were not affected by any colicin treatment (data not shown).

Discussion

In this study, colicin E1 was the most effective colicin. This result agrees with previous data indicating that colicin E1 displayed antimicrobial activity against several EHEC strains, not just O157:H7. Other E-type colicins were found to be suitable candidates as "biopreservatives" against E. coli O157:H7. However, other studies have indicated that the sensitivity of E. coli O157:H7 strains to any single colicin can be highly variable. For example, only 1 of 18 colicins examined inhibited all 540 E. coli O157:H7 strains screened. Because some E. coli O157:H7 strains are colicinogenic and produce specific concomitant immunity proteins, they can be resistant to certain colicins or even a broad category of colicins. Therefore, simultaneous administration of a mixture of several categories of colicins should be considered as a treatment concept to reduce E. coli O157:H7 (and other EHEC) in the gastrointestinal tract of food animals.

EXAMPLE 3

Recombinant Expression of Colicins

Yeast expression vectors were constructed and verified by sequencing for Colicin A, B, E1, 1a, and N. Expression and secretion of an active Colicin A by *Pichia pastoris* were obtained, and confirmed by spot testing of cell-free supernatant of *Pichia pastoris* expressing Colicin A against E. coli DH5α. In the functional assay (spot testing) 10 μl of cell-free supernatant from transformed *P. pastoris* showed a clearing of approximately the same size as 1 μg of purified Colicin A from *E. coli*. Spot 2 showed 1 μl of cell-free supernatant from *P. pastoris*. Spot 3 showed 5 μl of cell-free supernatant from *P. pastoris*, and spot 4 showed 10 μl of cell-free supernatant from *P. pastoris*.

EXAMPLE 5

Efficacy of Colicin E1 against *Listeria monocytogenes* FSIS 1126, H7769, Scott A, H7768, and H7767

Broth Culture Studies

Five isolated strains of *Listeria monocytogenes*, [one clinical isolate (Scott A) and four meat product isolates (FSIS 1126, H7769, H7762 and H7764)] which all carry the serotypes (½a, 4b) for human clinical illness, were grown and evaluated for sensitivity to colicin E1.

Inoculum Preparation

Growth studies were conducted to determine the optical density of cultures when they reached 10,000 CFU/ml. For each of the five cultures examined, frozen glycerol stock cultures (9.5 log CFU/ml) were thawed at room temperature, and 100 μl was added to 9 ml of sterile Trypticase soy broth containing 0.6% yeast extract (TSBYE). Cultures were then grown overnight at 37° C. Then 1 mL of this overnight growth was inoculated into 99 ml of fresh TSBYE and incubated at 37° C. The optical density at 600 nm (OD600) of the cultures and CFU/mL was determined hourly. Colony forming units (CFU)/mL were determined by serial dilution in peptone water followed by plating on Modified Oxford *Listeria* Selective Agar (MOX).

Testing for Sensitivity to Colicin E1

Pure cultures were inoculated from overnight growth into fresh TSBYE and allowed to grow to reach 10,000 CFU/ml. Aliquots (10 mL) were placed into culture tubes containing 0, 1, 10, or 100 μg of Colicin E1. This corresponds to doses of 0, 0.1, 1, and 10 μg/ml. The Colicin was a highly purified preparation that was provided at 1 mg Colicin E1/mL in 10 mM Tris, pH 7.6. The volume of each aliquot was made constant by the addition of 10 mM Tris, pH 7.6. Optical density (OD) was determined at 600nm, and was recorded hourly. CFU/mL were determined at 1, 3, and 6 hours post-inoculation. Colicin doses were provided at μg/mL of culture. The results are shown in FIGS. 12-16.

Discussion

All of the *L. monocytogenes* strains were sensitive to Colicin E1. Colicin E1 was more effective against H7767, H7768, and H7769 than against FSIS 1126 and Scott A. Complete inhibition of growth, for three to six hours, was obtained with only 0.1 μg/mL.

Ham Study #1-Scott A

Individual strain preparation: One mL of overnight growth of *L. monocytogenes* (Scott A) was inoculated into 99 ml of fresh TSBYE and allowed to grow to reach 1E7 (10,000, 000) CFU/ml.

Sample preparation: Sterilized ham slices (245 cm$^2$, 0.5 inch thick) were completely submerged in the *Listeria* culture for 10 min, and then transferred into sterile vacuum bags. One ml of 10 mM Tris, pH 7.6 containing 0, 10, or 50 μg Colicin E1 was placed into each bag and massaged using a stomacher for 60 seconds. Packages were then vacuum packaged and placed at refrigeration temperature (10° C.) for 3 days. On day 0, 1, 2 and 3, duplicate samples of colicin dose were pulled from refrigeration, aseptically cored (12.5 cm$^2$) and transferred to stomacher bag containing 25 ml 0.1% peptone water. Samples were mixed for 60 seconds, and then serially diluted, using 0.1 % peptone water, and plated onto MOX and incubated at 37° C. for 24 hours. Colonies from each sample on duplicate plates were counted and data were converted to log CFU/cm$^2$ of core isolated.

Figure 17:
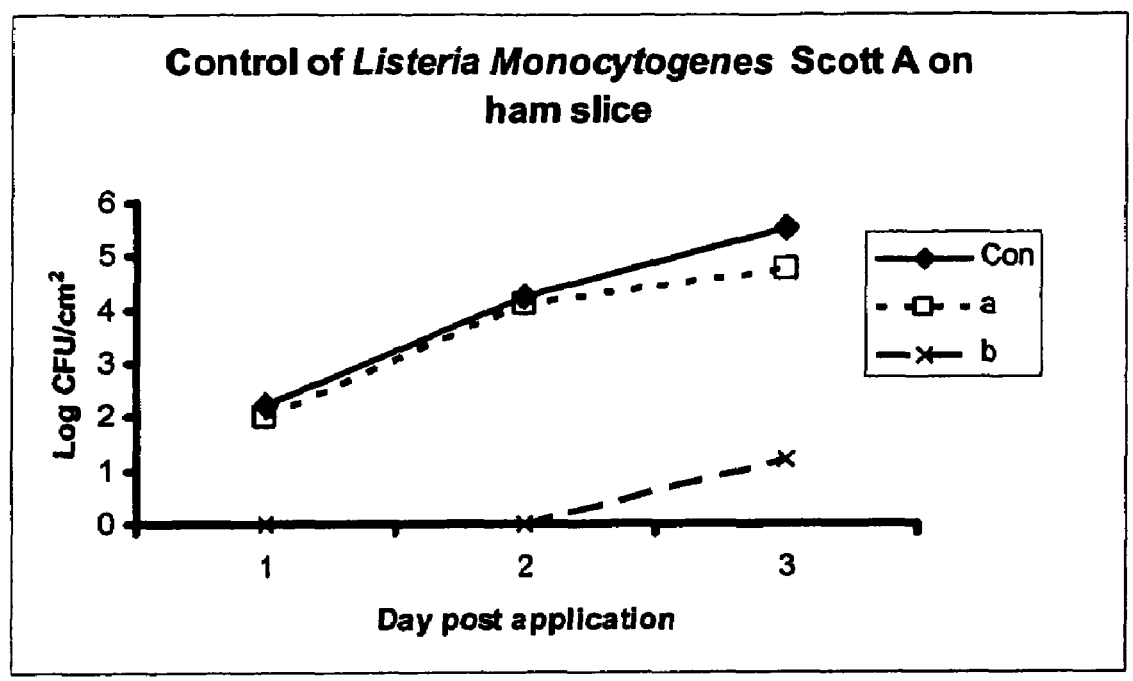
FIG. 17 illustrates the effect of Colicin E1 on the growth of *Listeria monocytogenes* strain Scott A on an uncured ham slice.

FIG. 17A depicts the CFU/cm$^2$ of Scott A on the uncured ham slice.

Ham Studies #2-5 Strain Cocktail

Inoculum Preparation: One mL of overnight growth of each of the five *Listeria* strains studied in the Broth Culture Studies was inoculated into 99 ml of fresh TSBYE and allowed to grow to reach either 1E8 (100,000,000) (High inoculum) or 1E5 (Low inoculum) CFU/ml. Ten ml of each culture was placed into 80 ml sterilized 0.1% peptone water and the five diluted cultures were then combined (450 ml) into a prex pan for submerging ham slices. This allowed for a cocktail inoculum that provided either 1E7 or 1E4 CFU/mL.

Sample preparation: Sterilized ham slices (232 cm$^2$, 0.5 inch thick) were sliced aseptically in half and placed into a prex pan containing the 5 strain *Listeria* cocktail. The ham slices were emerged totally for a period of 10 minutes, and then transferred into sterile vacuum bags. A total volume of 2 ml of 10 mM Tris, pH 7.6 containing either 0, 1, 10, or 50 μg/mL, was added to each bag and massaged using stomacher for 60 seconds. Packages were then vacuum packaged and placed at 4° C. for 3 days. On day 0, 1 and 3, duplicate samples of each inoculum level and colicin concentration were pulled from refrigeration, aseptically cored (12.5 cm$^2$) and transferred to stomacher bag containing 10 ml 0.1% peptone water. Samples were mixed for 60 seconds, and then serially diluted using 0.1% peptone water, plated on MOX and incubated at 37° C. for 24 hours. Colonies from each sample on duplicate plates were counted and data were converted to log CFU/cm$^2$ of core isolated.

Figure 18A:
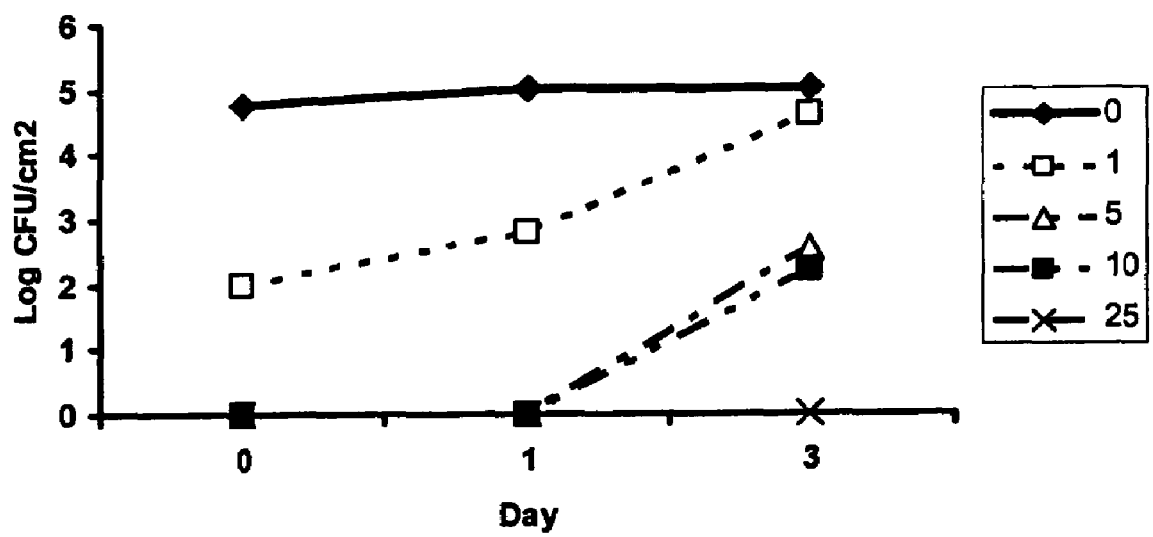
FIGS. 18A and 18B illustrate the effect of Colicin E1 on the growth of five *Listeria* strains on an uncured ham slice at high (A) and low (B) inoculum of *Listeria*.
Figure 18B:
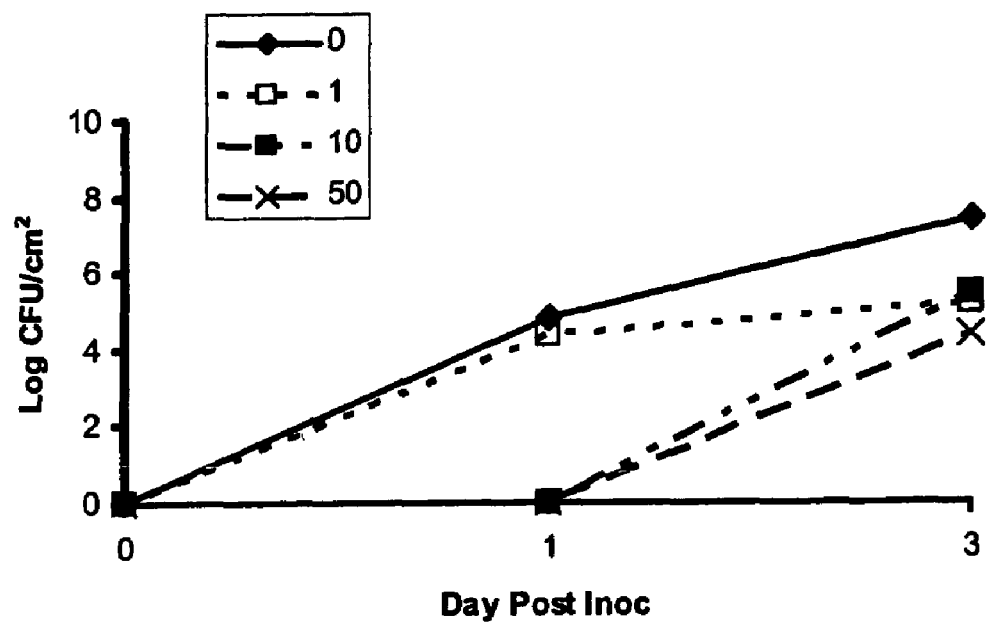

FIGS. 18A and 18B depict the CFU/cm$^2$ of the *Listeria* strain mixture on the uncured ham slice (2 log CFU=100 CFU).

The prophylactic use of antibiotics in animal agriculture has been greatly scrutinized in recent years, due to concerns regarding its role in contributing to antibiotic resistance. This scrutiny has led to increased regulation over the use of antibiotics in animal agriculture, and will likely continue towards a zero tolerance for the use of prophylactic or growth promoting antibiotic use in animals. With this regulatory milieu in mind, it is essential for the sustainability of animal agriculture to examine alternatives to conventional antibiotics to improve animal health and production efficiency. Because of their efficacy against *E. coli*, colicins are a viable alternative to conventional antibiotics in swine production. The present invention also demonstrates that colicins are highly effective against *Listeria* strains. The present invention demonstrates that colicins may be economically and readily synthesized using recombinant techniques.

For the above-stated reasons, it is submitted that the present invention accomplishes at least all of its stated objectives.

Having described the invention with reference to particular compositions and methods, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended.

What is claimed is:

1. A method of reducing *Listeria* on food comprising:
    applying a colicin to the food, said colicin selected from the group consisting of A, B, E1, 1a, and N.

2. The method of claim 1 whereby the colicin is applied to meat.

3. The method of claim 1 whereby the colicin is recombinant.

4. A method of reducing *Listeria* on food comprising:
    applying a colicin to the food, said colicin selected from the group consisting of E1 and N.

5. A method of reducing *Listeria* on food comprising:
    applying colicin E1 to the food.

* * * * *